US00PP13918P29

(12) United States Plant Patent
Austin

(10) Patent No.: US PP13,918 P2
(45) Date of Patent: Jul. 1, 2003

(54) SHRUB ROSE PLANT NAMED 'AUSCRYSTAL'

(75) Inventor: David C. H. Austin, Wolverhampton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 10/029,619

(22) Filed: Dec. 20, 2001

(51) Int. Cl.[7] ..... A01H 5/00
(52) U.S. Cl. ..... Plt./107
(58) Field of Search ..... Plt./107, 102, 137, Plt./148

(56) References Cited

PUBLICATIONS

UPOV–ROM GTITM Computer Database 2002/03, GTI Jouve Retrieval Software, Citation for Rosa 'Auscrystal'.*

* cited by examiner

*Primary Examiner*—Bruce R. Campell
*Assistant Examiner*—June Hwu
(74) *Attorney, Agent, or Firm*—Klarquist Sparkman LLP

(57) ABSTRACT

Shrub rose plant having warm, pale pink flowers; medium to dark green foliage with bronzy tinge; srong, almost prickleless, arching growth; and very flat, rosette-shaped flowers.

1 Drawing Sheet

Genus and Species: *Rosa hybrida.*
Varietal Denomination: 'AUScrystal'.

SUMMARY OF THE INVENTION

The present invention relates to a new and distinct variety of rose plant of the shrub class which was originated by me by crossing the variety 'AUSblush,' (unpatented), with an unnamed seedling (unpatented).

BACKGROUND OF THE INVENTION

The primary objective of this breeding was to produce a new rose variety having a very free-flowering and healthy growth with flowers of the classic English rose shape and with a good fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Warm, pale pink flowers;
2. Medium to dark green foliage with bronzy tinge;
3. Strong, almost thornless, arching growth; and
4. Very flat rosette-shaped flowers.

Asexual reproduction of this new variety by budding on *Rosa dumetorum laxa* rootstock, as performed at Albrighton, England, shows that the foregoing and all other characteristics and distinctions come true to form and are established and transmitted through succeeding propagations.

COMPARISON WITH PARENTS

'AUScrystal' plants have a strong, arching growth as compared to the more upright growth habit of 'AUSblush' and its flowers of about 130 petals are flat as compared the cupped shaped flowers of 'AUSblush' and the 50 petaled flower of the its pollen parent.

COMPARISON WITH SIMILAR VARIETY

The most similar variety, 'AUSglisten' (U.S. Plant Pat. No. 8,671), is more upright and branching and its foliage is smaller and rougher than that of 'AUScrystal'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:
*Seed parent.*—'AUSblush' (unpatented).
*Pollen parent.*—Unnamed Seedling (unpatented).

FLOWER

Observations made from plants of 8 years of age grown in a garden environment at Albrighton, England in July, 1998.

Blooming habit: Recurrent.
Bud:
*Size.*—About 0.6 inches long when the petals start to unfurl.
*Form.*—The bud form is short, globular.
*Color.*—When sepals first divide, bud color is: Upper surface: Red Group 56B and 56C. Lower surface:

Red Group 56C. When half blown: Upper surfaces of the petals are Red Group 56C; and the lower sides of the petals are Red Group 56C.

*Sepals.*—Color: Green Group 143C. Length: 0.8 inches. Width: 0.5 inches to 0.75 inches. Shape: Broadly ovate. Apex: Acuminate. Surface texture: Smooth with hairy edges. There are three normally appendaged sepals. There are two unappendaged sepals with hairy edges.

*Receptacle.*—Color: Green Group 143C with tint of Red-Purple Group 59A. Shape: Funnel. Size: Medium, about 0.2–0.3 inches×0.2–0.3 inches. Surface: Slightly hairy.

*Peduncle.*—Length: About 2 inches. Surface: Prickly. Color: Yellow-Green Group 144B with Red-Purple Group 59A blush on some. Strength: Stiff.

Blooms:

*Size.*—Medium. Average open size is 3 inches.

*Borne.*—In flat clusters of 3 to 7 blooms.

*Stems.*—Strength Normal. Average length is about 25–30 inches.

*Form.*—When first open bloom is: Flat. Permanence: Outer petals curl back.

*Petalage.*—Number of petals under normal conditions: 130.

*Color.*—The upper sides of the petals are Red Group 56C on upper portion and Red Group 56D in middle portion, and White Group 155B on the bottom portion. The major color on the upper side is Red Group 55C on inner petals and Red Group 56C on outer petals.

*Discoloration.*—The general tonality at the end of the first day: Red Group 55C. At the end of the third day: Red Group 55D. With aging the color changes to a bluing shade of pink.

*Fragrance.*—Strong. Character of fragrance: Old Rose.

Petals:

*Texture.*—Smooth.

*Shape.*—Orbicular and slightly quilled.

*Size.*—Length: 4.2 cm; Width: 4.0 cm.

*Margin.*—Undulate.

*Apex shape.*—Cuspidate.

*Base shape.*—Pointed.

*Form.*—Tips slightly recurved on outer petals, edges slightly quilled on inner petals.

*Arrangement.*—Irregular.

*Petaloids.*—Average number: 7. Size 1.5 mm width× 2.5 mm height. Color: Red Group RHS 55B. Shape: Elliptical.

*Persistence.*—Petals hang on and dry.

*Lastingness.*—On the plant: Long (15 days). As a cut flower: Not tested.

Reproductive parts:

*Stamens.*—Number: 64. Arrangement: Mixed with small leaves in flower center.

*Anthers.*—Length: 5/32 inch. Color: Yellow-Orange Group 14A.

*Filaments.*—Color: Yellow Group 4B. Length: 1/8 inch.

*Pollen.*—Color: Yellow-Orange Group 15A.

*Pistils.*—Number: 55. Styles: Color: Green-Yellow Group 1C. Length: 5 mm long. Stigmas: Color: Green-Yellow Group 1C. Length: 1 mm long.

*Hips.*—None formed.

Plant:

*Form.*—Shrub, (English style).

*Growth.*—Vigorous, arching.

*Mature plant.*—Height: 4.5 feet Width: 3.5 feet.

*Rootstock.*—'Dr. Huey' recommended for United States.

Foliage: Number of leaflets on normal mid-stem leaves: 5–7.

*Size.*—Large (5.5 inches long×3.75 inches wide).

*Quantity.*—Normal.

*Color.*—New foliage: Upper side: Yellow-Green Group 147A. Lower side: Yellow-Green Group 138A. Old foliage: Upper side: Green Group 139A. Lower side: Green Group 137A.

Leaflets:

*Size.*—About 2 inches long×2.25 inches wide.

*Shape.*—Broadly oval.

*Tip shape.*—Pointed.

*Base shape.*—Oblique and rounded.

*Texture.*—Smooth.

*Edge.*—Serrated.

*Serrations.*—Small.

*Petiole color.*—Greyed-Red Group 178A.

*Petiole rachis.*—Color: Yellow-Green Group 144A and Greyed-Purple Group 183C blush.

*Underside.*—Smooth.

*Auricle shape, if present.*—Long points.

*Stipules.*—Length: 0.75 inches, serrated.

*Disease resistance.*—Resistant to mildew, blackspot and rust under normal growing conditions.

*Pest resistance.*—Not tested.

Wood:

*New wood.*—Color: Greyed-Purple Group 183B and Yellow-Green Group 144B. Bark: Smooth.

*Old wood.*—Color: Yellow-Green Group 146B. Bark: Smooth.

Prickles:

*Quantity.*—On main canes from base: Top third of cane contains 15 prickles. On laterals from main canes: The bottom third of the cane contains 5 prickles).

*Form.*—Hooked downward. Length: 1/3 inch.

*Color when young.*—Greyed-Purple Group 184A.

*Color when mature.*—Greyed-Purple Group 185B.

Small prickles:

*Quantity.*—On main stalks: Few. On laterals: Few.

*Color.*—Violet Group 85B.

Climate hardiness: Hardy in Zones 4–9.

I claim:

1. A new and distinct variety of rose plant of the shrub class, substantially as herein shown and described, characterized particularly by warm, pale pink flowers; medium to dark green foliage with bronzy tinge; strong, almost prickleless, arching branches; and very flat, rosette-shaped flowers.

* * * * *

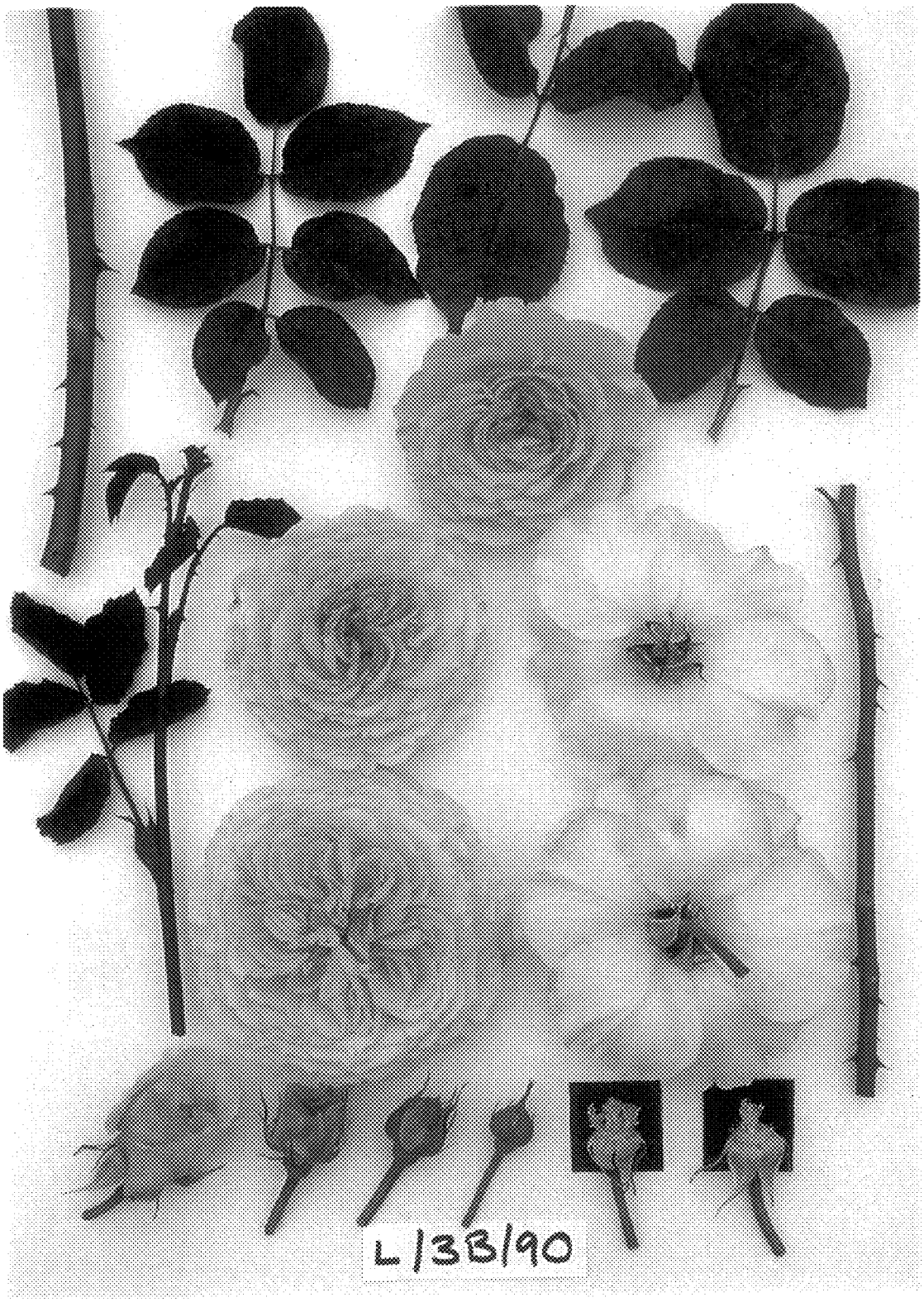
L/3B/90